(12) United States Patent
Niehren

(10) Patent No.: US 8,940,528 B2
(45) Date of Patent: Jan. 27, 2015

(54) PETRI-DISH FOR CELL CULTIVATION AND MICROSCOPY

(75) Inventor: Stefan Niehren, Altomünster (DE)

(73) Assignee: Molecular Machines & Industries AG, Glattbrugg (CH)

(*) Notice: Subject to any disclaimer, the term of this patent is extended or adjusted under 35 U.S.C. 154(b) by 55 days.

(21) Appl. No.: 13/126,933

(22) PCT Filed: Jul. 20, 2009

(86) PCT No.: PCT/IB2009/006283
§ 371 (c)(1),
(2), (4) Date: Apr. 29, 2011

(87) PCT Pub. No.: WO2009/127975
PCT Pub. Date: Oct. 22, 2009

(65) Prior Publication Data
US 2012/0015431 A1    Jan. 19, 2012

(30) Foreign Application Priority Data
Oct. 31, 2008 (DE) ................ 20 2008 014 487 U

(51) Int. Cl.
*C12M 1/22* (2006.01)
*G01N 1/28* (2006.01)
*B01L 3/00* (2006.01)

(52) U.S. Cl.
CPC ......... *C12M 23/10* (2013.01); *G01N 2001/284* (2013.01); *B01L 3/508* (2013.01)
USPC ................. 435/288.3; 435/40.52; 435/297.5

(58) Field of Classification Search
CPC ................. C12M 23/10; G01N 1/286; G01N 2001/2886
USPC ....................................... 435/305.4
See application file for complete search history.

(56) References Cited

U.S. PATENT DOCUMENTS 6,300,140 B1 * 10/2001 Robinson et al. ............ 436/518
7,318,999 B2 * 1/2008 Schutze ........................... 435/4
(Continued)

FOREIGN PATENT DOCUMENTS

| CN | 101245315 | * | 3/2008 |
| CN | 101245315 |   | 8/2008 |

(Continued)

OTHER PUBLICATIONS

International Search Report for Corresponding PCT Application PCT/IB2009/006283 mailed Nov. 18, 2009.
(Continued)

*Primary Examiner* — Michael Hobbs
*Assistant Examiner* — Liban Hassan
(74) *Attorney, Agent, or Firm* — Pabst Patent Group LLP

(57) ABSTRACT

A dish for cell cultivation and microscopy is provided, comprising a ring and an outer ridge upwardly and axially protruding therefrom, wherein the ring is covered at its bottom side with a transparent membrane and, thus, forms a recess delimited by the inner side of the ring and the membrane, characterized in that the recess is filled with an adhesive filling. Alternatively, a dish for cell cultivation and microscopy is provided, comprising a base and an outer ridge protruding upwardly and axially at its rim, wherein the base and the outer ridge are made of a transparent plastic, the base together with the inner side of the outer ridge forms a recess filled with an adhesive filling, and the thickness of the base and the filling together is less than about 1 mm.

15 Claims, 2 Drawing Sheets

(56) References Cited

U.S. PATENT DOCUMENTS

| | | | |
|---|---|---|---|
| 7,569,246 B2 * | 8/2009 | Schuetze et al. | 427/2.11 |
| 7,807,108 B2 * | 10/2010 | Fasulka | 422/400 |
| 2003/0032082 A1 | 2/2003 | Leclerc | |
| 2003/0180941 A1 | 9/2003 | Schutze | |
| 2005/0250219 A1 | 11/2005 | Schuetze | |
| 2006/0121298 A1 | 6/2006 | Wittke | |
| 2006/0223163 A1 * | 10/2006 | Sakai et al. | 435/285.1 |

FOREIGN PATENT DOCUMENTS

| | | | | |
|---|---|---|---|---|
| DE | 3102571 | | 9/1982 | |
| DE | 3102571 A1 * | | 9/1982 | C12M 1/22 |
| DE | 202004001703 | * | 5/2004 | C12M 1/26 |
| EP | 095231 | | 3/1999 | |
| JP | 06181740 | | 7/1994 | |
| JP | 11243949 | | 9/1999 | |
| JP | 200533938 | | 12/2005 | |
| JP | 2006194848 | | 7/2006 | |

OTHER PUBLICATIONS

"mmi Smart Cut Plus", User Manual, Molecular Machines & Industries AG (MMI), pp. 1-80 (2007).

"A cut above the rest:Olympus CellCut microdissection system", Olympus, pp. 1-12 (2006).

"Laser Microdissection system mmi SmartCut Plus/mmi Cellcut", Moleular machines & Industries AG (MMI) pp. 1-12.

* cited by examiner

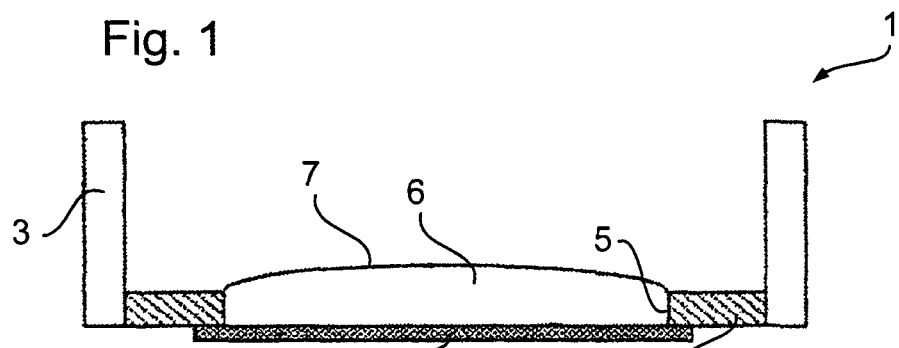
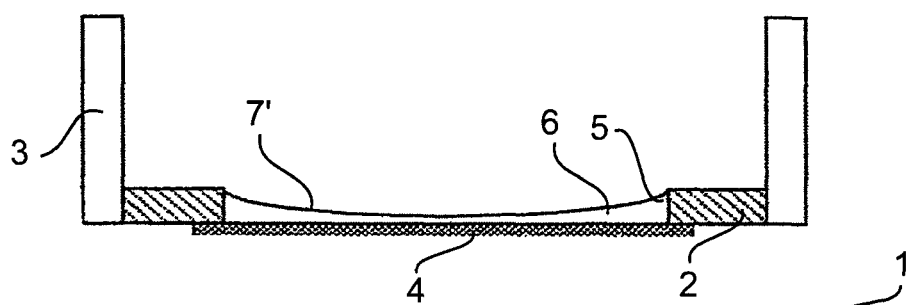
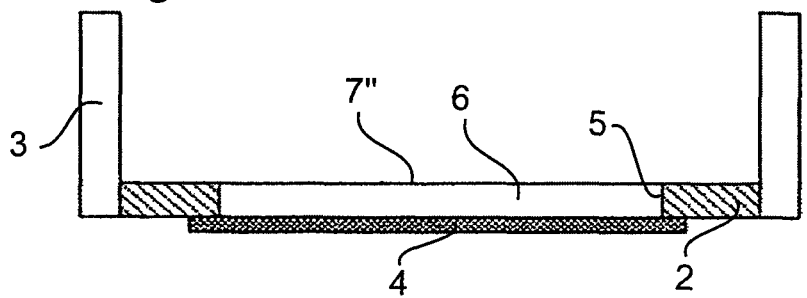
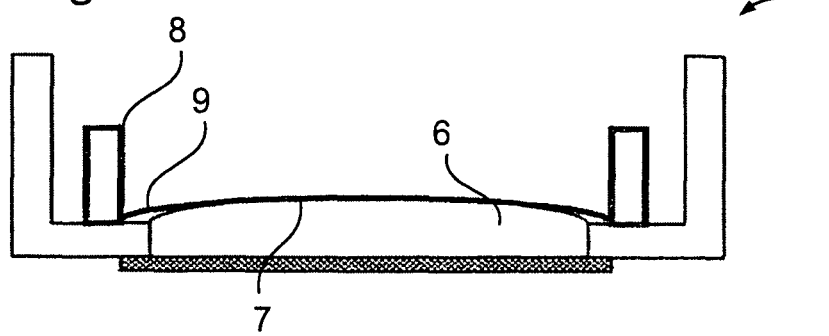

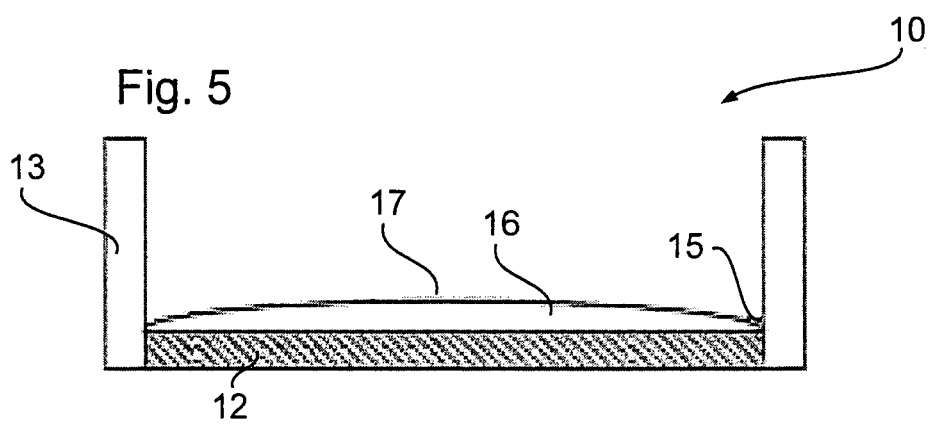

PETRI-DISH FOR CELL CULTIVATION AND MICROSCOPY

CROSS REFERENCE TO RELATED APPLICATIONS

This application is a national phase filing under 35 U.S.C. §371 of PCT/IB2009/006283 filed under the Patent Cooperation Treaty on Jul. 20, 2009, which claims priority to and benefit of foreign application DE 20 2008 014 487.6, filed on Oct. 31, 2008, the contents of each being hereby incorporated by reference in their entirety.

FIELD OF THE INVENTION

The present invention concerns a Petri dish for cell cultivation and microscopy, which can be utilized for cultivating cells as well as for observing the cultivated cells under a microscope, and which is particularly suited for performing laser dissection microscopy.

PRIOR ART

Hitherto, a combination of a silicone-coated glass Petri dish and a foil-covered metal ring was used for micro-dissection of living cells. The cells were cultivated in the membrane ring, then the ring was placed into the Petri dish and inserted into the microscope. The cells to be extracted were cut around their periphery by micro-dissection, and the ring was subsequently removed from the Petri dish. The cut-out cells remained in the Petri dish and were then further cultivated there.

The ring disclosed in DE 20 2004 001 703 U1 is to be mentioned as an example of a ring covered with a thin membrane, which in addition may comprise a protective membrane provided beneath the thin membrane and made of Teflon, for example.

The overall thickness of the bottom of the Petri dish having the ring and inserted into the microscope for laser micro-dissection is approximately two millimeters, a value which is borderline even for long distance objectives (20.times., 40.times.). Further, standard Petri dishes made of glass present strong geometric tolerances and, thus, strongly varying bottom thicknesses. Moreover, there is no controlled manufacturing process for silicone-filled glass Petri dishes that is capable to provide a precisely defined silicone insert and, thus, pre-determinable optical properties. Hence, this results in very bad microscopic properties of the silicone-filled glass Petri dishes so that these either cannot be used at all for modern microscopic methods such as phase contrast microscopy, fluorescence microscopy or DIC, or can only be used with strong restrictions on quality. Plastic Petri dishes that can be manufactured more easily and more precisely cannot be used for laser micro-dissection due to their poor UV transparency. Finally, a further problem consisted in the adhesion of the membrane on the silicone filling, which was either not present or not present over the entire surface.

SUMMARY OF THE INVENTION

Therefore, it is an object of the present invention to provide a dish for cell cultivation and microscopy, which offers exactly definable optical properties of its base and is suitable both for cell cultivation and for laser dissection microscopy as well. This object is achieved by means of a dish for cell cultivation and microscopy according to claim 1 or claim 8. Further preferred optional features are defined in the dependent claims.

SHORT DESCRIPTION OF THE FIGURES

FIG. 1 shows a dish of the invention having a ring and a convex adhesive filling;

FIG. 2 shows a dish having a ring and a concave adhesive filling;

FIG. 3 shows a dish having a ring and a flat adhesive filling;

FIG. 4 shows a dish according to the present invention, into which a laser micro-dissection membrane ring was inserted; and FIG. 5 shows a dish according to an alternative embodiment of the invention, which comprises a full-width base and a filling having a convex surface.

DETAILED DESCRIPTION OF PREFERRED EMBODIMENTS

In FIG. 1, an inventive Petri dish 1 according to a first embodiment of the invention is illustrated. The dish comprises a ring 2 forming a part of the base, to which an outer ridge or rim 3 of the dish, extending on the outside and upwardly in an axial direction, is connected. The ring and the outer ridge are preferably made from an optically transparent material such as silica glass (fused quartz glass) or an optically transparent plastic and may be manufactured in one piece (integrally), or separately and then joined. In particular if the ring and/or the outer ridge are made of plastic, a high manufacturing precision and a constant product quality may be achieved by injection molding, for example, which are a pre-requisite for using the dish in microscopy. The thickness of the ring is preferably around one millimeter, which corresponds to the thickness of conventional microscope object slides.

At the bottom side of the ring 2 a bottom membrane 4 is attached, the thickness of which is substantially smaller than the thickness of the bottom ring 2, and which closes off the ring opening from below. The bottom membrane is made of a material transparent for UV radiation, such as special compositions of polystyrene and polypropylene. Preferably, the membrane may also be a cover glass that may be made of ultrapure silica glass (fused quartz glass), for example. The thickness of the membrane 4 or the cover glass is preferably less than 500.mu.m, and is preferably 100.mu.m.

The inner side 5 of the ring forms, together with the bottom membrane 4, a recess, the depth of which corresponds to the thickness of the ring and is, thus, about 1 mm. The recess is filled with an adhesive filling 6 transparent to UV radiation and preferably made of silicone so that a preferably slightly convex surface 7 is formed. In this way, a transparent bottom surface is formed which, on the one hand, is adapted to the thickness of microscope object slides, is optically highly transparent and at the same time maximizes the adhesion surface with a membrane ring to be placed into the dish by virtue of its convex configuration. As the adhesive filling 6 is spatially defined by the recess, easy manufacturing is ensured. Besides, in this way the thickness of the bottom layer may be adapted to the thickness of standardized microscope object slides so that the inventive dish may be utilized directly with conventional microscope objectives. The UV transparency of the filling and the membrane or cover glass is, in particular, necessary for procedures in which the dissected objects are cut from samples held in the dish by means of a UV laser.

FIGS. 2 and 3 show alternative embodiments of the inventive Petri dish, wherein the surface 7' of the adhesive filling in FIG. 2 is concave and the surface 7" in FIG. 3 is flat. While the concave filling is particularly suited for applications in which low amounts of buffer are necessary, the flat filling lends itself for applications in which only shallow (narrow) depths of field, preferably at large microscopic magnifications, are allowed and a curvature of the sample is, thus, disadvantageous.

In the embodiments of FIGS. 1 to 3, the thickness of the filling approximately corresponds to the one of the recess, i.e. about 1 millimeter, though this is strictly true only for the flat embodiment of FIG. 3 and, for the embodiments of FIGS. 1 and 2, variations of this thickness in a radial direction of the dish due to the surface shape (convex or concave) need to be taken into account, so that a variation in the range of 500.mu.m to 1,200.mu.m is to be considered.

In FIG. 4, the inventive dish having a convex filing and a laser micro-dissection (LMD) membrane ring 8 placed therein is shown. As can be seen from the figure, the LMD membrane 9 is tensioned (spanned) over the convex-shaped surface 7 of the adhesive filling 6 and therefore adheres to it over its entire surface. Hence, due to the adhesion the cells present on the cut LMD membrane after laser cutting cannot be displaced so that a higher degree of referenceability is achieved.

Finally, FIG. 5 shows an embodiment in which a Petri dish 10 comprises a base (bottom) 12 and an outer ridge or rim 13 of the dish, extending upward at its rim in an axial direction. Here, the base and the outer ridge are made of plastic, the latter being transparent for the base and, according to the specific application, transparent or opaque for the outer ridge. Together with the inner side 15 of the outer ridge, the base forms thus a recess which, like in the above embodiments, is filled with an adhesive filling 16 transparent to UV radiation and preferably made of silicone, so that a preferably slightly convex surface 17 is created. The thickness of the base and filling together is less than about 1 mm. The transparent bottom surface formed in this way provides the same advantages as the embodiment of FIG. 1, but can be manufactured even more easily.

The dishes described in the above embodiments are particularly suitable for interference contrast microscopy, phase contrast microscopy, fluorescence methods and laser micro-dissection.

The invention claimed is:

1. A system for cell cultivation and laser dissection microscopy, comprising: (a) a dish and (b) a ring insert covered with a laser-microdissection membrane, wherein the dish comprises
(i) a base, and
(ii) an outer ridge,
wherein the base comprises a recess defined by:
(1) a ring comprising a top surface, a bottom surface, an outer surface and an inner surface, and
(2) a transparent membrane comprising a top surface and a bottom surface,
wherein the top surface of the transparent membrane is attached to the bottom surface of the ring and defines a bottom surface of the recess,
wherein the recess is filled with an adhesive filling,
wherein the outer ridge of the dish protrudes upwardly and axially from the outer surface of the ring, and
wherein when the ring insert is placed in the dish, the adhesive filling adheres to the laser micro-dissection membrane.

2. The system according to claim 1, wherein the transparent membrane is cover glass.

3. The system according to claim 1, wherein the transparent membrane is transparent to ultraviolet radiation.

4. The system according to claim 1, wherein the thickness of the transparent membrane is less than 500 μm.

5. The system according to claim 1, wherein the thickness of the filling and the transparent membrane together is less than about 1 mm.

6. The system according to claim 1, wherein the thickness of the ring is about 1 mm.

7. The system according to claim 1, wherein the ring and the outer ridge are made of a transparent material.

8. The system according to claim 1, wherein the surface of the adhesive filling in the recess is concave.

9. The system according to claim 1, wherein the surface of the adhesive filling in the recess is convex.

10. The system according to claim 1, wherein the surface of the adhesive filling in the recess is flat.

11. The system according to claim 1, wherein the filling is a polymer material or a gel.

12. The system according to claim 1, wherein the adhesive filling is transparent to ultraviolet radiation.

13. The system according to claim 7, wherein the ring and the outer ridge are made of a transparent plastic.

14. The system according to claim 11, wherein the polymer material is a silicone.

15. The system of claim 1, wherein the ring insert protrudes upwardly and axially from the laser-microdissection membrane.

* * * * *